United States Patent [19]

Behre et al.

[11] Patent Number: 4,859,372

[45] Date of Patent: Aug. 22, 1989

[54] PROCESS FOR THE SULPHONATION OF AROMATIC COMPOUNDS WITH SULPHUR TRIOXIDE

[75] Inventors: Horst Behre, Odenthal-Eikamp; Heinz U. Blank, Odenthal; Wilfried Köhler, Cologne; Nikolaus Müller, Leverkusen; Peter Schnegg, Odenthal, all of Fed. Rep. of Germany

[73] Assignee: Bayer Aktiengesellschaft, Leverkusen, Fed. Rep. of Germany

[21] Appl. No.: 296,396

[22] Filed: Jan. 6, 1989

Related U.S. Application Data

[63] Continuation of Ser. No. 636,457, Jul. 31, 1984, now abandoned.

[30] Foreign Application Priority Data

Aug. 23, 1983 [DE] Fed. Rep. of Germany ....... 3330334

[51] Int. Cl.$^4$ ........................................... C07C 143/24
[52] U.S. Cl. ...................................... 562/74; 562/88; 562/90

[58] Field of Search ........... 260/505 R, 505 C, 505 E, 260/513 T

[56] References Cited

PUBLICATIONS

Groggins, Unit Processes in Org. Synth., 4th ed., pp. 296–297, (1952).
Gilbert, Sulfonation & Related Reactions, (1965), pp. 18–19.

Primary Examiner—Alan Siegel
Attorney, Agent, or Firm—Sprung Horn Kramer & Woods

[57] ABSTRACT

A new process for the preparation of aromatic sulphonic acids, in which the sulphonation of the aromatic compounds is carried out with sulphur trioxide in organic solvents in the presence of hydrogen halide.

3 Claims, No Drawings

PROCESS FOR THE SULPHONATION OF AROMATIC COMPOUNDS WITH SULPHUR TRIOXIDE

This application is a continuation of application Ser. No. 636,457, filed July 31, 1984, now abandoned.

The invention relates to a new process for the preparation of aromatic sulphonic acids by sulphonation of aromatic compounds with sulphur trioxide.

The preparation of aromatic sulphonic acids by sulphonation of aromatic compounds with sulphur trioxide is known (see, for example, E. E. Gilbert, Chemical Review 62 (1962) pages 549–589). The disadvantage of the use of sulphur trioxide as the sulphonating agent is that considerable amounts of undesired by-products, which are frequently difficult to remove, are formed in these sulphonation reactions because of the high reactivity of the sulphur trioxide.

Substantially more gentle sulphonation with sulphur trioxide is achieved if the reactivity of the sulphur trioxide is reduced by complexing it with ethers, such as dioxane, tertiary amines, such as pyridine, or carboxylic acid amides, such as dimethylformamide. The sulphonation reactions with these sulphur trioxide complexes proceed substantially more selectively, that is to say with the formation of fewer by-products, but they have the series disadvantage, especially for sulphonation reactions on an industrial scale, that the complexing agents obtained in stoichiometric amounts must be recovered, for reasons of cost and of pollution of the effluent, or, if they have not recovered, lead to serious pollution of the effluent and hence at least partly destroy again the advantage which sulphonation with sulphur trioxide offers per se.

Chlorosulphonic acid has also already been used as the sulphonating agent instead of the reactive sulphur trioxide. As a result of its weaker sulphonating action in comparison with sulphur trioxide, an improved selectivity and hence a reduction in the formation of by-products is achieved with chlorosulphonic acid, especially in the sulphonation of aromatic compounds which are easy to sulphonate. However, the use of chlorosulphonic acid as the sulphonating agent has the serious disadvantage that stoichiometric amounts of hydrogen chloride are obtained as a by-product and these must be destroyed, that is to say rendered harmless by neutralisation, since they cannot be reused for the preparation of chlorosulphonic acid, because of the enormous technical expenditure which is combined with such reuse. This means that although chlorosulphonic acid per se is an advantageous sulphonating agent for sensitive aromatic compounds, its use for sulphonation reactions on an industrial is precluded by: (a) its substantially higher price, compared with the price of sulphur trioxide, and (b) the high costs associated with rendering the hydrogen chloride formed in equimolar amounts in the sulphonation harmless.

Surprisingly, it has been found that hydrogen halide is an excellent agent for reducing the reactivity of sulphur trioxide. It has been found that the reactivity of sulphur trioxide is reduced by hydrogen halide to the extent that it is now possible for even sensitive aromatic compounds which, because they are easy to sulphonate, require gentle sulphonation, to be sulphonated collectively in outstanding yields with sulphur trioxide. It has been found that the reactivity of the sulphur trioxide can be adapted to the ease of sulphonation of the aromatic compounds to be sulphonated by establishing a certain hydrogen halide concentration in the reaction mixture.

The invention thus relates to a process for the sulphonation of aromatic compounds with sulphur trioxide in inert organic solvents, which is characterised in that the sulphonation is carried out in the presence of hydrogen halide.

Hydrogen chloride is preferably used as the hydrogen halide. The hydrogen halide can be added to the sulphonation mixture as such, for example as gaseous hydrogen chloride, or in the form of compounds which split off or form hydrogen halide in the reaction mixture under the reaction conditions. An example of such a compound which forms hydrogen halide (hydrogen chloride) in the reaction mixture under the reaction conditions is chlorosulphonic acid.

The hydrogen halide can be added to the compound to be sulphonated before the sulphur trioxide is added or at the same time as the sulphur trioxide.

The deactivating effect of the hydrogen halide depends on the amount in which it is employed; the larger the amount of hydrogen halide, the greater the deactivation of the sulphur trioxide. As a result, larger amounts of hydrogen halide are employed in the sulphonation of particularly sensitive aromatic compounds which are easy to sulphonate than in the sulphonation of less sensitive aromatic compounds which are less easy to sulphonate. For the sulphonation of particularly sensitive aromatic compounds, it may be appropriate to employ more than one mol of hydrogen halide per mol of sulphur trioxide. In general, however, it is sufficient to employ the hydrogen halide in sub-stoichiometric amounts (based on the sulphur trioxide), for example in an amount of 0.01–0.9 mol, preferably 0.1–0.8 mol and in particular 0.25–0.75 mol, of hydrogen halide per mol of sulphur trioxide for the desired deactivation of the sulphur trioxide.

The process according to the invention is particularly suitable for selective monosulphonation of aromatic compounds which are easy to sulphonate, such as naphthalene, 1-methylnaphthalene, 2-hydroxynaphthalene and diphenyl. These compounds are sulphonated selectively in high yields with the aid of the process according to the invention to give naphthalene-1-sulphonic acid, 1-methylnaphthalene-4-sulphonic acid, 2-hydroxynaphthalene-1-sulphonic acid and diphenyl-4-sulphonic acid.

Whilst in the working up of sulphonation mixtures which are obtained in the sulphonation of aromatic compounds with chlorosulphonic acid the equimolar amounts of hydrogen chloride formed in the reaction must be destroyed or must be converted into pure hydrogen chloride or pure hydrochloric acid, which can be further used, or into chlorosulphonic acid by means of expensive processes, the hydrogen halide-containing sulphonation mixtures obtained in the process according to the invention are worked up such that the hydrogen halide is not lost but is recovered, for example, together with the organic solvent and reused in the next batch.

The process according to the invention is thus of great industrial importance, because it permits selective sulphonation of sensitive aromatic compounds with sulphur trioxide without foreign compounds, such as complexing agents or hydrogen chloride, which must be either recovered or rendered harmless, being liberated or formed during the sulphonation. Apart from the desired aromatic sulphonic acids and negligibly small amounts of by-products, no foreign compounds at all are formed in the process according to the invention. The hydrogen halide is recovered and reused in the next batch.

Suitable inert organic solvents for the process according to the invention are those solvents which do not react, or at least do not react to a noticeable degree, with sulphur trioxide under the reaction conditions and which at the same time have a good dissolving capacity for the hydrogen halide. Examples of such solvents are aliphatic halogenohydrocarbons, such as tetrachloroethane, 1,2-dichloroethane and 1,2-dichloropropane. Methylene chloride has proved particularly suitable.

The process according to the invention is carried out at temperatures from $-40°$ to $+20°$ C., preferably $-30°$ to $+10°$ C. and in particular $-20°$ to $0°$ C.

The sulphur trioxide can be used in the process according to the invention in liquid or gaseous form or in the form of a solution in the inert organic solvent. Gaseous sulphur trioxide, if appropriate diluted with an inert gas, such as nitrogen, or solutions of sulphur trioxide in methylene chloride are preferably used.

The sulphonation process according to the invention can be carried out in various ways; for example by dissolving or suspending the aromatic compound to be sulphonated, for example naphthalene, in the inert organic solvent, for example methylene chloride, and passing the hydrogen halide, for example hydrogen chloride, into the solution or suspension until the solution or suspension has taken up the desired amounts of hydrogen halide. The sulphur trioxide is then added. The sulphonation can be carried out either under normal pressure or under increased pressure. Various stationary hydrogen halide concentrations can be established in the reaction mixture during the addition of sulphur trioxide by suitable choice of the parameters of pressure and temperature and of an inert organic solvent with the desired dissolving capacity for the hydrogen halide.

Another embodiment consists in adding the hydrogen halide and the sulphur trioxide simultaneously to a solution or suspension of the aromatic compound to be sulphonated in the organic solvent.

A third procedure comprises producing the hydrogen halide required for the process according to the invention directly in the reaction mixture, for example by first partially sulphonating the aromatic compound with chlorosulphonic acid in the inert organic solvent, care being taken that the hydrogen chloride formed remains in the reaction mixture, and then bringing the sulphonation to completion by adding the amount of sulphur trioxide required for the complete sulphonation. Instead of adding all the chlorosulphonic acid at the start, it is also possible first to add only some of the chlorosulphonic acid in this embodiment and, when this has reacted to form hydrogen chloride, to meter in the remaining amount of chlorosulphonic acid at the same time as the amount of sulphur trioxide required for the sulphonation.

The sulphonic acids, such as naphthalene-1-sulphonic acid, 2-hydroxynaphthalene-1-sulphonic acid and diphenyl-4-sulphonic acid, obtainable by the process according to the invention are important precursors and intermediates for the preparation of dyestuffs, plant protection agents and emulsifiers (see, for example, Ullmanns Enzyklopädie der technischen Chemie (Ullman's Encyclopaedia of Industrial Chemistry), 4th Edition, Volume 17, pages 117 and 94 and Volume 18, page 219).

EXAMPLE 1

64.1 g (0.5 mol) of naphthalene are dissolved in 250 ml of anhydrous methylene chloride in a 1-liter sulphonating apparatus. The solution is cooled to $-20°$ C. 9.2 g (0.25 mol) of hydrogen chloride gas are first passed into the resulting suspension in the course of about 30 minutes, with stirring. 40 g (0.5 mol) of gaseous sulphur trioxide are then passed onto the surface of stirred naphthalene/methylene chloride suspension by means of dry nitrogen in the course of 1 hour, likewise with stirring at $-20°$ C. The reaction mixture is then stirred at $-20°$ C. for 2 hours and subsequently poured into 500 g of an ice-water mixture.

The methylene chloride phase is separated off, extracted 2 times with 250 ml of water each time and concentrated to dryness in vacuo. According to analysis by gas chromatography, the residue (5.9 g) contains 73.2% by weight of naphthalene (=6.7% of the naphthalene employed).

The combined aqueous phases are briefly subjected to incipient distillation in vacuo to remove residues of methylene chloride, and are transferred to a 1-liter measuring flask and made up to 1 liter.

High pressure liquid chromatography (HPLC) of this solution shows the following content of naphthalenesulphonic acids: 89.0 g of naphthalene-1-sulphonic acid (=85% of theory, based on the naphthalene employed; =91.8% of theory based on the naphthalene reacted), 6.2 g of naphthalene-2-sulphonic acid (=6.0% of theory), based on the naphthalene employed; =6.5% of theory, based on the naphthalene reacted) and 0.4 g of naphthalene-disulphonic acids (=0.28% of theory, based on the naphthalene employed; =0.3% of theory, based on the naphthalene reacted).

The sulphonation was repeated as described above, with the only difference that no hydrogen chloride was passed in. The yields of naphthalenesulphonic acids (in % of theory, based on the naphthalene reacted) in this case were: 76.0% of naphthalene-1-sulphonic acid, 8.4% of naphthalene-2-sulphonic acid, 0.4% of naphthalene-1,3-disulphonic acid, 10.4% of naphthalene-1,5-disulphonic acid, 2.7% of naphthalene-1,6-disulphonic acid and 0.6% of naphthalene-1,7-disulphonic acid.

EXAMPLE 2

The procedure followed was as described in Example 1, except that the hydrogen chloride and sulphur trioxide were metered in simultaneously.

The yields of naphthalene-sulphonic acids (in % of theory, based on the naphthalene reacted) were: 90.4% of naphthalene-1-sulphonic acid, 7.3% of naphthalene-2-sulphonic acid and 0.3% of naphthalene-disulphonic acids.

EXAMPLE 3

The procedure followed was as described in Example 1, except that the reaction was carried out in a more diluted solution (the 64.1 g of the naphthalene were dissolved in 500 ml of methylene chloride).

In this procedure, the yields of naphthalene-sulphonic acids (in % of theory, based on the naphthalene reacted) were: 89.9% of naphthalene-1-sulphonic acid, 9.8% of naphthalene-2-sulphonic acid and 0.5% of naphthalene-disulphonic acids.

EXAMPLE 4

A solution of 25.6% (0.2 mol) of naphthalene in 250 ml of dry methylene chloride is cooled to −20° C. in the sulphonating apparatus described in Example 1. Dry hydrogen chloride is passed through the solution at a rate of 8 liters/hour, and at the same time a solution, cooled to −10° C., of 16 g (0.2 mol) of sulphur trioxide in 150 ml of dry methylene chloride is added at −20° C. in the course of 2 hours, with cooling and stirring.

The reaction mixture is subsequently stirred at −20° C. for 2 hours and is then worked up as described in Example 1.

According to HPLC, the yield of naphthalene-sulphonic acid (in % of theory, based on the naphthalene reacted) is: 89.0% of naphthalene-1-sulphonic acid, 10.0% of naphthalene-2-sulphonic acid, 0.6% of naphthalene-1,5-disulphonic acid and 0.2% of naphthalene-1,6-disulphonic acid.

EXAMPLE 5

A solution of 25.6 g (0.2 mol) of naphthalene in 250 g of dry methylene chloride is cooled to −20° C. in the sulphonating apparatus described in Example 1. At −20° C., with stirring, a solution of 18 g (0.15 mol) of chlorosulphonic acid in 50 g of dry methylene chloride is first allowed to run in over a period of 10 minutes, and a solution, cooled to −10° C., of 4 g (0.05 mol) of sulphur trioxide in 50 g of dry methylene chloride is then allowed to run in over a period of 20 minutes. The reaction mixture is subsequently stirred at −20° C. for 2 hours and is then worked up as described in Example 4.

According to HPLC, the yield of naphthalene-sulphonic acids (in % of theory, based on the naphthalene reacted) is: 91.0% of naphthalene-1-sulphonic acid, 8.6% of naphthalene-2-sulphonic acid, 0.1% of naphthalene-1,5-disulphonic acid and 0.1% of naphthalene-1,6-disulphonic acid.

When the chlorosulphonic acid solution and sulphur trioxide solution were added simultaneously, the yield of naphthalene-sulphonic acids (in % of theory, based on the naphthalene reacted) was: 89.7% of naphthalene-1-sulphonic acid, 9.2% of naphthalene-2-sulphonic acid, 0.7% of naphthalene-1,5-disulphonic acid and 0.3% of naphthalene-1,6-disulphonic acid.

EXAMPLE 6

The procedure followed was as described in Example 5, except that a solution of 12 g (0.1 mol) of chlorosulphonic acid and 8 g (0.1 mol) of sulphur trioxide in each case in 50 g of methylene chloride were added dropwise in the course of 30 minutes and, respectively, 90 minutes instead of the chlorosulphonic acid and sulphur trioxide solutions used in Example 5.

According to HPLC, the yield of naphthalene-sulphonic acids (in % of theory, based on the naphthalene reacted) was: 89.0% of naphthalene-1-sulphonic acid, 10.3% of naphthalene-2-sulphonic acid, 0.3% of naphthalene-1,5-disulphonic acid and 0.2% of naphthalene-1,6-disulphonic acid.

EXAMPLE 7

154 g (1.00 mol) of diphenyl are dissolved in 1,000 ml of anhydrous methylene chloride in a 2-liter sulphonating apparatus. 7.3 g (0.20 mol) of hydrogen chloride gas are passed into the solution at −10° C., with stirring. 77 g (0.96 mol) of gaseous sulphur dioxide are then passed onto the surface of the solution of diphenyl and hydrogen chloride in methylene chloride in the course of 2 hours, likewise with stirring at −10° C. The reaction mixture is subsequently stirred at −10° C. for 1 hour. The sulphonation mixture is worked up as described in Example 1.

According to HPLC, the yield of diphenyl-sulphonic acids (in % of theory, based on the diphenyl reacted) is: 99.4% of diphenyl-4-sulphonic acid and 0.5% of diphenyl-4,4'-disulphonic acid.

EXAMPLE 8

A solution of 30.8 g (0.2 mol) of diphenyl in 250 g of dry methylene chloride is reacted, as described in Example 4, with a solution, cooled to −10° C., of 16 g (0.2 mol) of sulphur trioxide in dry methylene chloride, while passing through about 8 liters/hour of dry hydrogen chloride. The sulphonation mixture is worked up as described in Example 4.

According to HPLC, the yield of diphenyl-sulphonic acids (in % of theory, based on the diphenyl reacted) is: 98.3% of diphenyl-4-sulphonic acid and 0.7% of diphenyl-4,4'-disulphonic acid.

EXAMPLE 9

28.8 g (0.2 mol) of 2-hydroxynaphthalene are dissolved in 300 g of dry methylene chloride at 40° C. in the sulphonating apparatus described in Example 1. The solution is cooled to −20° C. Dry hydrogen chloride is uniformly passed through the resulting suspension at a rate of 8 liters/hour, and at the same time, a solution, cooled to −10° C., of 16 g (0.2 mol) of sulphur trioxide in 50 g of dry methylene chloride is added at −20° C. in the course of about 1 hour, with cooling and stirring. The reaction mixture is then subsequently stirred at −20° C. for 2 hours and is then poured into about 100 g of an ice-water mixture, whilst maintaining a temperature below 20° C. A pH value of 7 is established in the 2-phase reaction mixture obtained in this manner, by addition of 50% strength sodium hydroxide solution. After the methylene chloride phase has been separated off, the aqueous phase is freed from residues of solvent by incipient distillation in vacuo and is transferred to a measuring flask and made up to 1 liter with water.

According to HPLC, the yields of 2-hydroxynaphthalenesulphonic acids (in % of theory, based on the 2-hydroxynaphthalene reacted) are: 92.8% of 2-hydroxynaphthalene-1-sulphonic acid, 0.5% of 2-hydroxynaphthalene-5-sulphonic acid, 0.5% of 2-hydroxynaphthalene-6-sulphonic acid, 3.0% of 2-hydroxynaphthalene-8-sulphonic acid and 0.6% of 2-hydroxynaphthalene-1,6-disulphonic acid.

No other 2-hydroxynaphthalene-sulphonic acids were to be detected in the reaction mixture.

If the sulphonation of 2-hydroxynaphthalene described above was carried out in the absence of hydrogen chloride, the following yields of 2-hydroxynaphthalenesulphonic acids (in % of theory, based on the 2-hydroxynaphthalene reacted) were obtained: 83.5% of 2-hydroxynaphthalene-1-sulphonic acid, 2.1% of 2-hydroxynaphthalene-5-sulphonic acid, 0.4% of 2-hydroxynaphthalene-6-sulphonic acid, 6.9% of 2-hydroxynaphthalene-8-sulphonic acid, 1.0% of 2-hydroxynaphthalene-1,6-disulphonic acid and 0.4% of 2-hydroxynaphthalene-6,8-disulphonic acid.

EXAMPLE 10

A solution of 64.1 g (0.5 mol) of naphthalene in 250 ml of anhydrous methylene chloride is cooled to −20°

C. in a 1-liter sulphonating beaker, which is provided with a bottom outlet, into the top of this outlet a glass frit being incorporated. Dry hydrogen chloride is passed into the resulting suspension at −20° C. until saturation is achieved (that is to say until about 15 g of HCl have been taken up). 40 g (0.5 mol) of sulphur trioxide are then passed onto the surface of the suspension of naphthalene in methylene chloride containing hydrogen chloride at −20° C. in the course of about 1.5 hours, with stirring. After the reaction mixture has been subsequently stirred at −20° C. for 2 hours, the precipitate is isolated from the mother liquor containing hydrogen chloride, by forcing this mother liquor through the frit and the bottom outlet into a second, similarly equipped 1-liter sulphonating beaker by means of dry nitrogen, and the precipitate on the frit is rinsed with 50 ml of dry methylene chloride.

The composition of the methylene chloride-moist product which has been filtered off with suction was determined by HPLC; it was: 91.6% by weight of naphthalene-1-sulphnonic acid, 2.3% by weight of naphthalene-2-sulphonic acid and 0.6% by weight of naphthalene-disulphonic acids.

The solution of filtrate and washing solution combined in the second sulphonating beaker is cooled to −20° C. and 64.1 g (0.5 mol) of finely powdered naphthalene are added. Dry hydrogen chloride is again passed into the suspension until saturation is achieved (about 4 g of HCl are required here). The sulphonation is then carried out as in the preceding batch by passing sulphur trioxide onto the surface of the stirred suspension of naphthalene in methylene chloride containing hydrogen chloride. When the reaction has ended, the mother liquor is again forced into the first sulphonating beaker by means of dry nitrogen, and the product on the frit is washed with fresh dry methylene chloride.

The composition of the methylene chloride-moist product was determined by means of HPLC; it was: 86.4% by weight of naphthalene-1-sulphonic acid, 4.1% by weight of naphthalene-2-sulphonic acid and 0.3% by weight of naphthalene-disulphonic acids.

In this semi-continuous procedure, the yields of sulphonic acids (in % of theory, based on the naphthalene reacted) after the saturation concentration had been established for the individual sulphonic acids in the mother liquor, that is to say after the 5th batch, are, per batch: 91.7% of naphthalene-1-sulphonic acid, 6.2% of naphthalene-2-sulphonic acid and 0.3% of naphthalene-disulphonic acids.

What is claimed is:

1. In a process for the preparation of an aromatic sulfonic acid by sulfonation of an aromatic compound wherein the sulfonating agent consists of sulfur trioxide and the sulphonation is carried out in an aliphatic halogenohydrocarbon, the improvement which comprises carrying out the sulphonation in the presence of 0.01 to 0.9 moles of hydrogen halide per mol of sulfur trioxide at temperatures from −40° to +20° C.

2. The process of claim 1, wherein the hydrogen halide is hydrogen chloride.

3. The process of claim 1, wherein the organic solvent is methylene chloride.

* * * * *